United States Patent [19]

Kersten

[11] 4,411,661

[45] Oct. 25, 1983

[54] SPIKE CONNECTOR

[75] Inventor: Jean Kersten, Villers St. Amand, Belgium

[73] Assignee: Travenol European Research and Development Centre, Brussels, Belgium

[21] Appl. No.: 399,511

[22] Filed: Jul. 19, 1982

Related U.S. Application Data

[63] Continuation of Ser. No. 199,140, Oct. 22, 1980, abandoned.

[51] Int. Cl.³ .......................... B67B 7/24; A61M 5/16
[52] U.S. Cl. .................................... 604/411; 222/81; 222/567; 604/251
[58] Field of Search ................. 222/81, 83, 83.5, 88, 222/567; 220/85 SP; 604/251, 252, 411, 414

[56] References Cited

U.S. PATENT DOCUMENTS

| | | |
|---|---|---|
| D. 229,518 | 12/1973 | Bujan . |
| 2,453,133 | 11/1948 | Jones .................................. 222/81 |
| 2,552,155 | 5/1951 | Danielson ............................ 222/81 |
| 2,598,843 | 6/1952 | Sherwood ............................ 222/81 |
| 2,746,455 | 5/1956 | Abel . |
| 2,751,119 | 6/1956 | Manning, Jr. ....................... 222/81 |
| 2,989,053 | 6/1961 | Hamilton . |
| 3,831,814 | 8/1974 | Butler ................................. 222/81 |
| 3,868,965 | 3/1975 | Noiles et al. .................... 128/214 C |
| 4,162,220 | 7/1979 | Servas ............................. 128/214 C |
| 4,173,223 | 11/1979 | Raines et al. ................... 128/214 C |

FOREIGN PATENT DOCUMENTS

| | | |
|---|---|---|
| 2221564 | 11/1973 | Fed. Rep. of Germany . |
| 7702734 | 9/1977 | Fed. Rep. of Germany . |
| 2758518 | 7/1978 | Fed. Rep. of Germany . |
| 601688 | 3/1926 | France ................................. 222/81 |
| 2375870 | 7/1978 | France . |
| WO80/02506 | 11/1980 | PCT Int'l Appl. . |

*Primary Examiner*—David A. Scherbel
*Attorney, Agent, or Firm*—John P. Kirby, Jr.; George H. Gerstman; Bradford R. L. Price

[57] ABSTRACT

A spike connector (10) of the type in which a hollowed spike (14) extending from the main body portion (12) of the spike connector is inserted into the stopper of a fluid source in order to convey the fluid from the source through the spike (14) and main body portion (12). The main body portion (12) includes a pair of wings (32, 34) which extend upwardly in the direction of the spike and outwardly therefrom, with the tops of the wings serving to space the remaining top of the main body portion (12) away from the fluid source stopper to prevent collection of the solution on the top of the main body portion. The undersides (36, 38) of the wings (32, 34) form a convenient finger grip. The tip portion (30) of the spike is relatively polished to enable easy insertion of the spike into the stopper.

12 Claims, 6 Drawing Figures

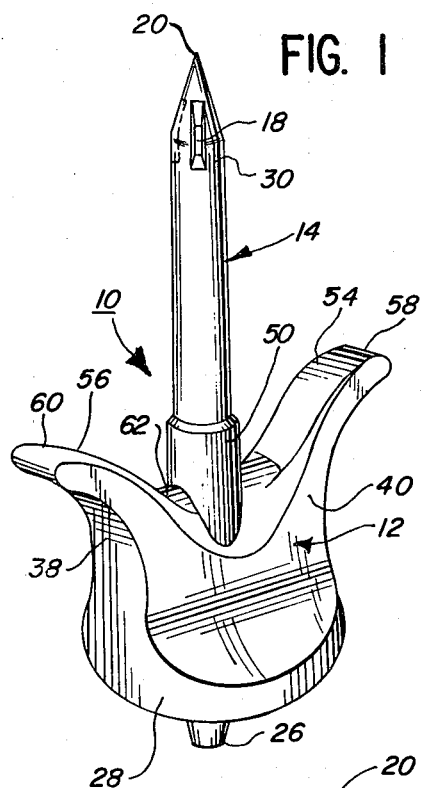
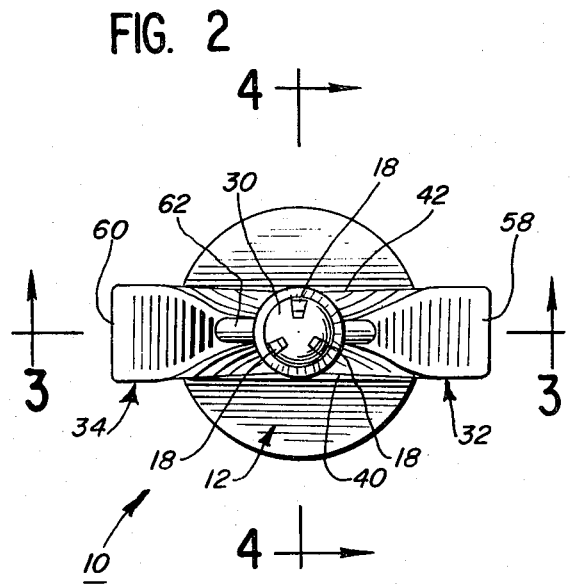
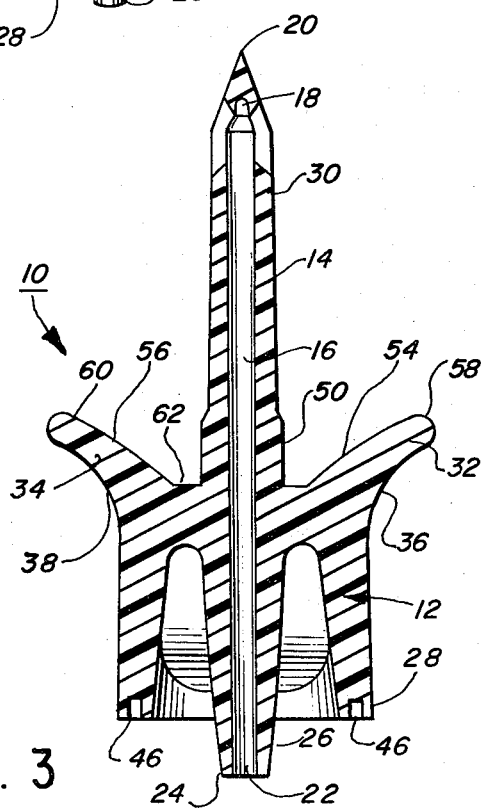
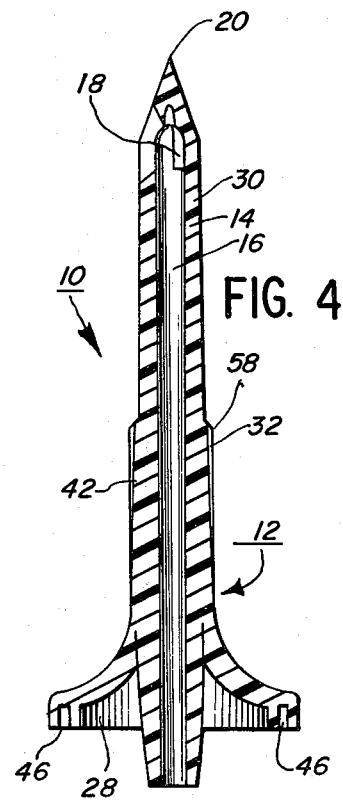

FIG. 5
FIG. 6
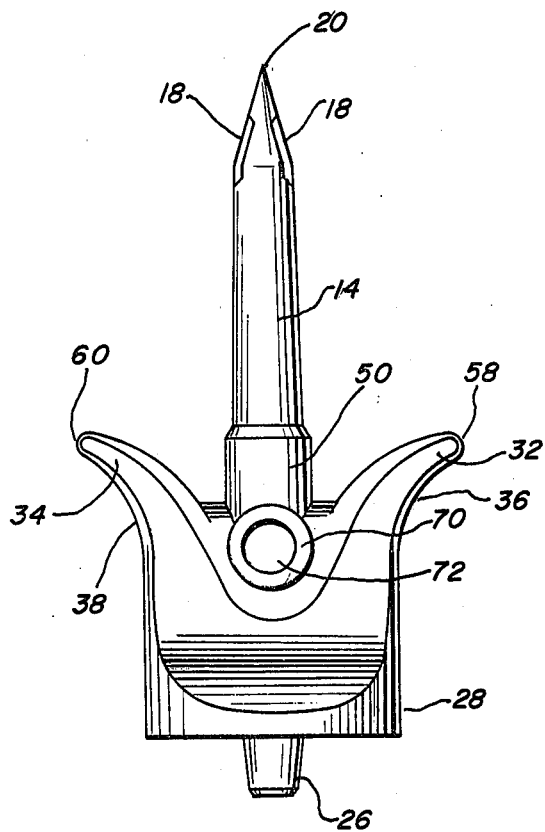
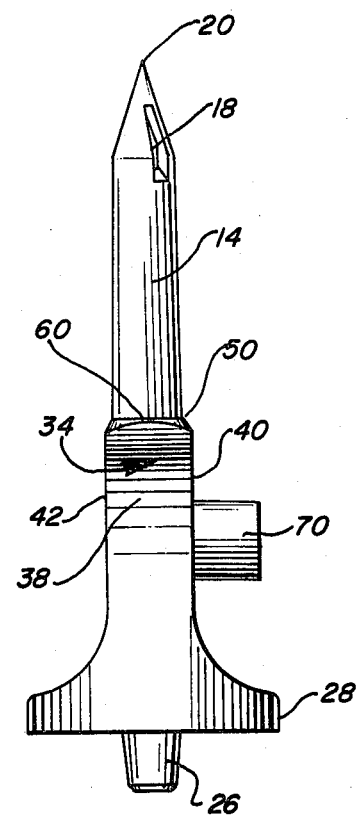

SPIKE CONNECTOR

This application is a continuation of United States application Ser. No. 199,140, filed Oct. 22, 1980 now abandoned.

BACKGROUND ART

Known in the art are integrally molded spike connectors for coupling a drip chamber to the stopper of a fluid source. An example of one type of spike connector, commonly referred to as an airway connector, is illustrated in U.S. Pat. No. Des. 229,518, issued Dec. 4, 1973. Other spike connectors, primarily for use with collapsible plastic containers, do not utilize a filtered airway.

The configuration of certain prior art spike connectors has made it difficult for an operator to have access to the stopper once the spike of the spike connector has been inserted into the stopper. For example, while certain stoppers carry an injection site, some prior art spike connectors overlie the injection site and block the injection site from the operator once the spike of the spike connector is inserted into the stopper.

Certain prior art spike connectors are configured to become relatively flush with the stopper once the spike is inserted into the stopper. This flush engagement may be deleterious because a leaking liquid may collect on the surface which engages the stopper. One prior art type of spike connector, licensed by American Hospital Supply Corporation in Italy, has a flat surface which engages the stopper with the flat surface forming the periphery of an open volume. This enables the collection of solution on the flat surface and in the open volume, and thereby increases chances of contamination.

DISCLOSURE OF INVENTION

It is an object of the present invention to provide a spike connector in which the main body portion has only an extremely small amount of contact with the stopper so as to avoid surface area which may carry contaminants.

Another object of the present invention is to provide a spike connector that enables relatively good access to an injection site on the stopper, after the spike of the spike connector is inserted into the stopper.

A further object of the invention is to provide a spike connector that has a main body portion with a very small amount of contact with the stopper, enables relatively good access to an injection site carried by the stopper, yet is relatively efficient in its use of plastic.

Another object of the present invention is to provide a spike connector that has a spike which enters easily into the stopper but maintains frictional compression with the stopper once the spike is fully inserted thereinto.

Other objects and advantages of the invention will become apparent as the description proceeds.

In accordance with the present invention, a spike connector is provided having a main body portion and a hollowed spike extending therefrom for insertion into the stopper of a fluid source and for conveyance of the fluid from the source through the spike and main body portion. The main body portion includes a pair of wings which extend upwardly in the direction of the spike but outwardly therefrom. The wings extend away from each other. The undersides of the wings are arcuately constructed to enable an operator to grasp the main body portion at the undersides. The tops of the wings serve to space other than the wing tops away from the fluid source stopper when the spike is inserted into the stopper.

In the illustrative embodiment, the spike connector is molded in an integral, one-piece construction, with each wing forming an included angle of about 45° between the wing and the axis of the spike. The main axis of both wings and the spike are coplanar.

In the illustrative embodiment, the spike has a relatively polished surface adjacent its tip as compared to the surface adjacent the main body portion, in order to enable easy insertion of the spike into the stopper but good frictional engagement of the spike with the stopper once the spike is fully inserted into the stopper.

A more detailed explanation of the invention is provided in the following description and claims, and is illustrated in the accompanying drawings.

BRIEF DESCRIPTION OF DRAWINGS

FIG. 1 is a perspective view of a spike connector constructed in accordance with the principles of the present invention.

FIG. 2 is a top plan view thereof.

FIG. 3 is a cross-sectional elevation thereof, taken along the plane of the line 3—3 of FIG. 2.

FIG. 4 is a cross-sectional elevation thereof, taken along the plane of the line 4—4 of FIG. 2.

FIG. 5 is a front elevational view of an airway connector forming a modified embodiment of the present invention.

FIG. 6 is a side elevational view thereof.

DETAILED DESCRIPTION OF THE ILLUSTRATIVE EMBODIMENTS

Referring to FIGS. 1-4, a spike connector 10 is shown therein having a main body portion 12 and a hollowed spike 14 extending from the main body portion. The hollowed spike 14 is adapted for insertion into the stopper of a fluid source, such as a parenteral liquid container in the form of a collapsible plastic container. Main body portion 12 and spike 14 define a bore 16 which extends from an opening 18 adjacent spike tip 20 to outlet opening 22 at the distal end 24 of drip tube 26, for conveying the fluid from the container through opening 18, via bore 16 and through outlet opening 22, typically to a drip chamber that is connected to the bottom 28 of main body portion 12.

Spike connector 10 is preferably molded of polypropylene in an integral, one-piece construction. When the molding is completed, a surface area 30 from tip 20 downward to between about 1.0 centimeter and 1.5 centimeter, is polished. This provides surface 30 with a relatively polished, smooth surface finish in contrast to the surface finish of the remainder of the spike, thereby allowing relatively easy entry of the spike into the stopper but providing good retention of the spike within the stopper once it is inserted, by reason of the frictional compression provided by the less polished lower portion.

Main body portion 12 includes a pair of wings 32, 34 each of which extends upwardly in the direction of the spike 14 but outwardly therefrom, preferably forming an included angle of about 45° between the respective wing and the spike axis. In the illustrative embodiment, the main axes of both wings 32 and 34, and the axis of spike 14 are coplanar.

Main body portion 12 has four sides 36, 38, 40 and 42. Sides 36 and 38 form the undersides of wings 32 and 34, respectively, and are arcuate to provide an economically and functionally shaped comfortable finger guard to sides 36 and 38 and the top portions thereof are narrow and generally planar while the bottom portions of sides 40 and 42 curve outwardly away from the spike. The bottom 28 of main body portion 12 has a generally circular cross-sectional configuration perpendicular to the spike, and a slot 46 is provided to receive the top portion of the drip chamber. Drip tube 26 has an outlet opening 22 that provides a drop rate of about 20 drops per minute.

The lower portion 50 of spike 14 has a greater external diameter, so that the spike may be utilized with containers having a larger than normal stopper opening. In the illustrative embodiment, spike 14 is provided with three equally spaced openings 18 about the spike tip and in communication with bore 16.

Top surfaces 54 and 56 of wings 32 and 34, respectively, are smooth and curved to avoid dust and fluid collection. Wing tips 58 and 60 are spaced a relatively great distance from lower surface 62 and tips 58 and 60 will be the only contact points of the main body portion against the stopper when the spike is inserted into the stopper. This substantial lack of surface contact between the main portion and the stopper is useful in preventing the collection of leaking liquid on the main body portion. In addition, by utilizing extending wings 32 and 34, bottom 28 of the main body portion 12 is at a relatively far distance away from the stopper, without having to utilize a substantial amount of plastic, and enabling the operator to have relatively good access to an injection site carried by the stopper. By utilizing top portions of sides 40 and 42 that are relatively flat surfaces, the operator may write on such flat surface with a marking pen, if so desired, while the curved lower surface of sides 40 and 42 enable easy removal of the spike connector from the stopper.

It can be seen that wings 32 and 34 in cooperation with the lower portion of the main body portion operate to provide a finger grip that is efficiently designed for easy insertion and removal of the spike connector from the stopper. At the same time, wings 32 and 34 are operable to prevent touch contamination of the stopper. Further, the relatively narrow sides 40 and 42 plus the distance of the bottom of the main body portion from the top thereof aid in enabling the operator to have good access to an injection site carried by the stopper for supplementary medication additions or use of a separate airway. Still further, the wings have very small contact points with the stopper when a spike is inserted into the stopper, and thus contamination by reason of the liquid pooling along the top of the main body portion is alleviated.

An airway connector, constructed in accordance with the principles of the present invention, is illustrated in FIGS. 5 and 6. Identical reference numerals are used in FIGS. 5 and 6 for structural components which are identical to those utilized in the FIGS. 1-4 embodiment. However, the airway connector of FIGS. 5 and 6 utilizes a spike 14 which carries a separate fluid bore and airway bore, with the airway bore communicating with a filtered airway opening 70. Although airway opening 70 is illustrated at a right angle with respect to spike 14, it is to be understood that the airway opening may extend at other than a right angle with respect to spike 14. The airway opening 17 surrounds a hydrophobic airway filter 72, preferably formed of Porex filter material. A cap or plug may be utilized to close and seal airway 70 when the airway is not used, for example, when the connector is issued with a collapsible plastic container.

All of the benefits and the results concomitant with the spike connector described in connection with FIGS. 1-4 are also concomitant with respect to the airway spike connector described in connection with FIGS. 5 and 6.

Although illustrative embodiments of the invention have been shown and described, it is to be understood that various modifications and substitutions may be made by those skilled in the art without departing from the novel spirit and scope of the present invention.

That which is claimed is:

1. A spike connector having a main body portion and a hollowed spike extending therefrom for insertion into the stopper of a fluid source and for conveyance of the fluid from the source through the spike and main body portion, the improvement comprising:
    said main body portion including a pair of wings extending upwardly in the direction of said spike but outwardly therefrom, said pair of wings extending away from each other, the undersides of said wings being arcuately constructed to enable an operator to grab said main body portion at said undersides, and the tops of said wings serving to space other than said wing tops away from the fluid source stopper when the spike is inserted into the stopper;
    said main body portion having a generally circular cross-sectional configuration perpendicular to said spike and at the end thereof that is distal from said spike, and means adjacent the circular cross-sectional portion for receiving a drip chamber.

2. A spike connector as described in claim 1, said spike connector being molded of polypropylene in an integral, one-piece construction.

3. A spike connector as described in claim 1, each wing forming an included angle of about 45° between the wing and the axis of the spike.

4. A spike connector as described in claim 1, wherein the main axes of both wings and the spike are coplanar.

5. A spike connector having a main body portion and a hollowed spike extending therefrom for insertion into the stopper of a fluid source and for conveyance of the fluid from the source through the spike and main body portion, the improvement comprising:
    said main body portion including a pair of wings extending upwardly in the direction of said spike but outwardly therefrom, said pair of wings extending away from each other, the undersides of said wings being arcuately constructed to enable an operator to grab said main body portion at said undersides, and the tops of said wings serving to space other than said wing tops away from the fluid source stopper when the spike is inserted into the stopper;
    the main body portion having four sides, two sides of the main body portion forming the undersides of the wings and the other two sides of the main body portion being narrow and generally planar adjacent the spike but curving outwardly away from the spike.

6. A spike connector as described in claim 5, said main body portion having a generally circular cross-sectional configuration perpendicular to said spike and at the end thereof that is distal from said spike, and means adjacent the circular cross-sectional portion for receiving a drip chamber.

7. A spike connector having a main body portion and a hollowed spike extending therefrom for insertion into the stopper of a fluid source and for conveyance of the fluid from the source through the spike and main body portion, the improvement comprising:

said main body portion including a pair of wings extending upwardly in the direction of said spike but outwardly therefrom, said pair of wings extending away from each other, the undersides of said wings being arcuately constructed to enable an operator to grab said main body portion at said undersides, and the tops of said wings serving to space other than said wing tops away from the fluid source stopper when the spike is inserted into the stopper;

said spike having a relatively polished surface adjacent its tip as compared to the surface adjacent said main body portion.

8. A spike connector as described in claim 7, said relatively polished surface extending from 1.0 centimeter to 1.5 centimeter from said tip.

9. A spike connector formed in an integral, one-piece construction and having a main body portion and a hollowed spike extending therefrom for insertion into the stopper of a fluid source and for conveyance of the fluid from the source through the spike and main body portion, the improvement comprising:

said main body portion including a pair of wings extending upwardly in the direction of said spike but outwardly therefrom, said pair of wings extending away from each other with the main axis of both wings and the spike being coplanar, said main body portion having four sides with two sides of the main body portion forming undersides of the wings and with the other two sides of the main body portion being narrow and generally planar adjacent the spike but curving outwardly away from the spike, said undersides of said wings being arcuately constructed to enable an operator to grasp said main body portion at said undersides, and the tops of said wings serving to space other than said wing tops away from the fluid source stopper when the spike is inserted into the stopper, said main body portion having a generally circular cross-sectional configuration perpendicular to said spike and at the end thereof that is distal from said spike, and means adjacent the circular cross-sectional portion for receiving a drip chamber.

10. A spike connector as described in claim 9, wherein each wing forms an included angle of about 45° between the wing and the axis of the spike.

11. A spike connector as described in claim 9, said spike having a relatively polished surface adjacent its tip as compared to the surface adjacent said main body portion, said relatively polished surface extending from 1.0 to 1.5 centimeter from said tip.

12. A spike connector having a main body portion and a hollowed spike extending therefrom for insertion into the stopper of a fluid source and for conveyance of the fluid from the source through the spike and main body portion, the improvement comprising:

said spike having a relatively polished surface adjacent its tip as compared to the surface adjacent said main body portion, said relatively polished surface extending from 1.0 centimeter to 1.5 centimeter from said tip, whereby insertion of the spike into the stopper is simplified while greater frictional compression is provided once the spike is inserted into the stopper.

* * * * *